United States Patent [19]

Podoloff et al.

[11] Patent Number: 5,033,291
[45] Date of Patent: Jul. 23, 1991

[54] FLEXIBLE TACTILE SENSOR FOR MEASURING FOOT PRESSURE DISTRIBUTIONS AND FOR GASKETS

[75] Inventors: Robert M. Podoloff, Framingham; Michael H. Benjamin, Quincy; Jay Winters, Andover; Robert F. Golden, Boston, all of Mass.

[73] Assignee: Tekscan, Inc., Boston, Mass.

[21] Appl. No.: 448,127

[22] Filed: Dec. 11, 1989

[51] Int. Cl.$^5$ .................. A61B 5/00; G01M 19/00
[52] U.S. Cl. ........................................ 73/172; 73/865.7
[58] Field of Search .................. 73/172, 865.7, 862.07

[56] References Cited

U.S. PATENT DOCUMENTS

| | | | |
|---|---|---|---|
| 4,426,884 | 1/1984 | Polchanioff | 73/172 |
| 4,503,705 | 3/1985 | Polchanioff | 73/172 |
| 4,734,034 | 3/1988 | Maness et al. | 73/865.7 X |
| 4,856,993 | 8/1989 | Maness et al. | 73/865.7 |

Primary Examiner—Daniel M. Yasich
Attorney, Agent, or Firm—Wolf, Greenfield & Sacks

[57] ABSTRACT

A force and pressure sensor is provided having two sets of parallel electrodes which are positioned facing one another and arranged so that electrodes of one set cross the electrodes of the second set at an angle to create a plurality of electrode intersections. Pressure-sensitive resistive material lies between the electrodes at each intersection. An adhesive layer is applied to at least one of the electrode sets in areas between electrode intersections to secure the first and second electrode sets in facing relationship, the adhesive layer preferably being applied in a pattern which provides passages where the adhesive layer does not exist to allow air to escape from interior areas of the electrode set. The thickness of the adhesive layer may be adjusted to permit preloading or to provide a threshold level for the sensor. In order to permit electrodes of the electrode set to be trimmed around their periphery, electrical contact to each electrode of the electrode sets is made intermediate the ends of the electrodes. This is accomplished by providing an insulating layer over the rear of each electrode set having holes therein at the desired intersection points and having a plurality of connecting conductors on the back of the insulating sheet, one for each electrode, which make contact with the corresponding electrode through the hole in the insulating sheet.

18 Claims, 4 Drawing Sheets

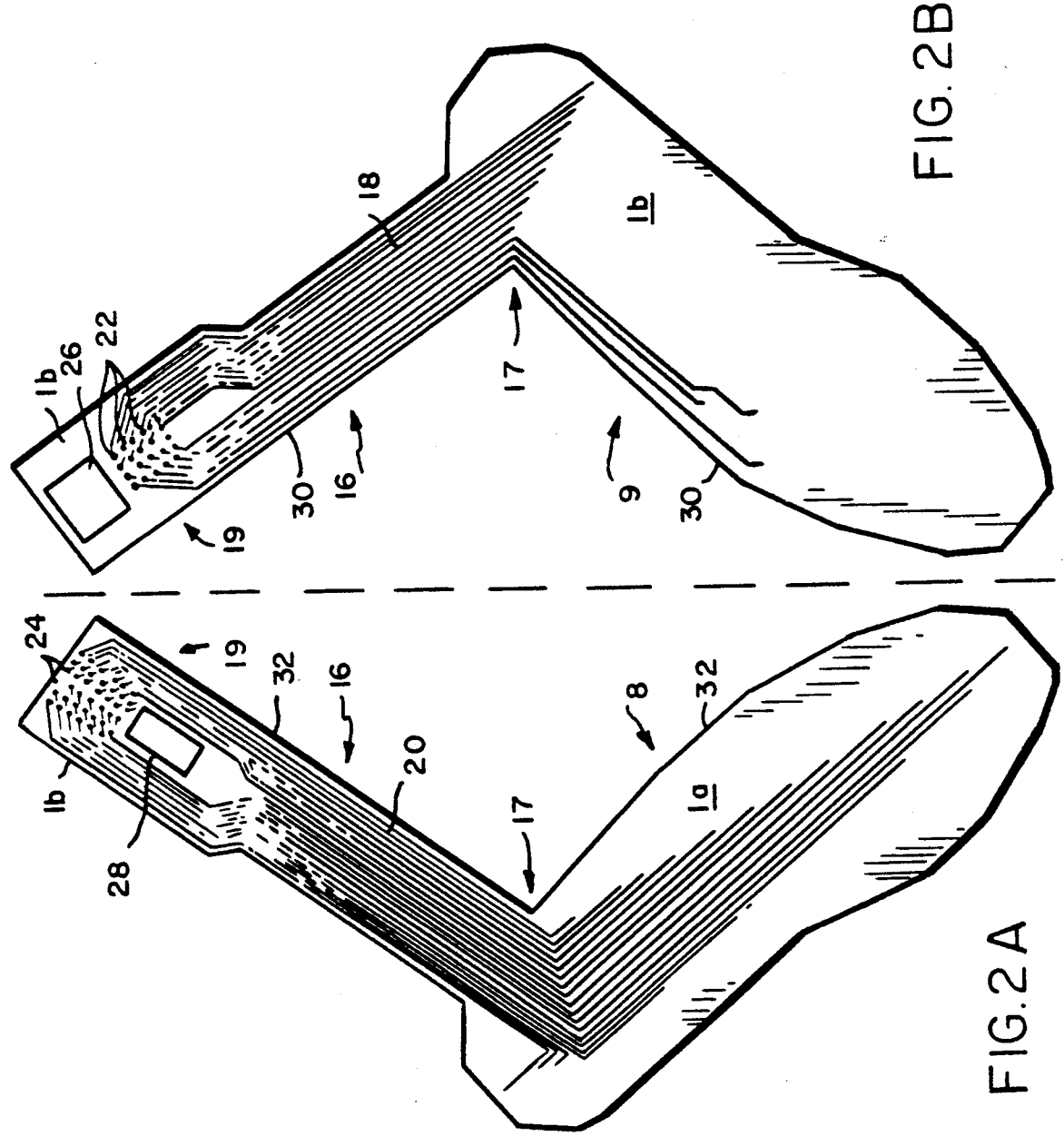

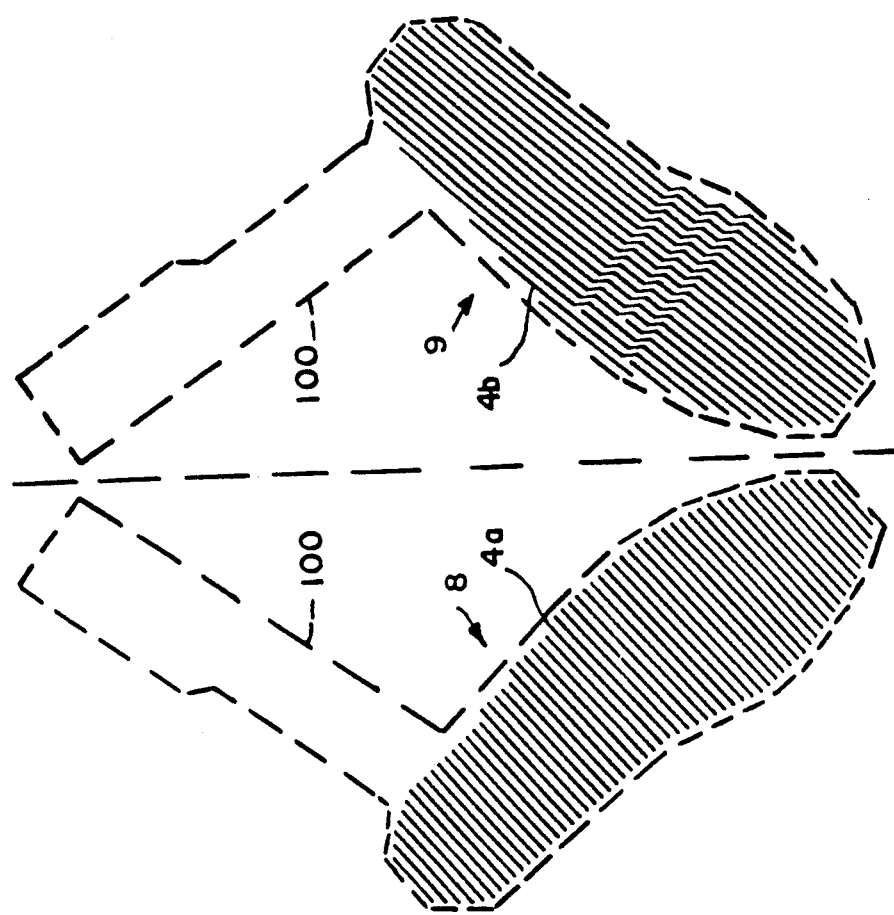
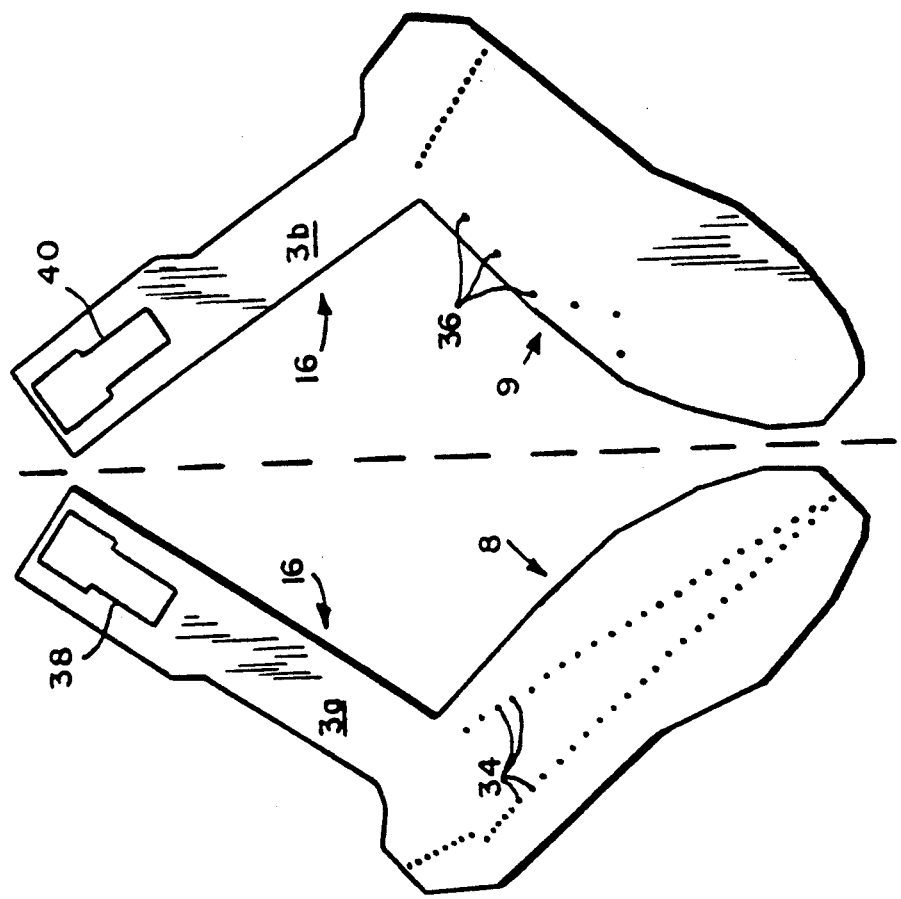

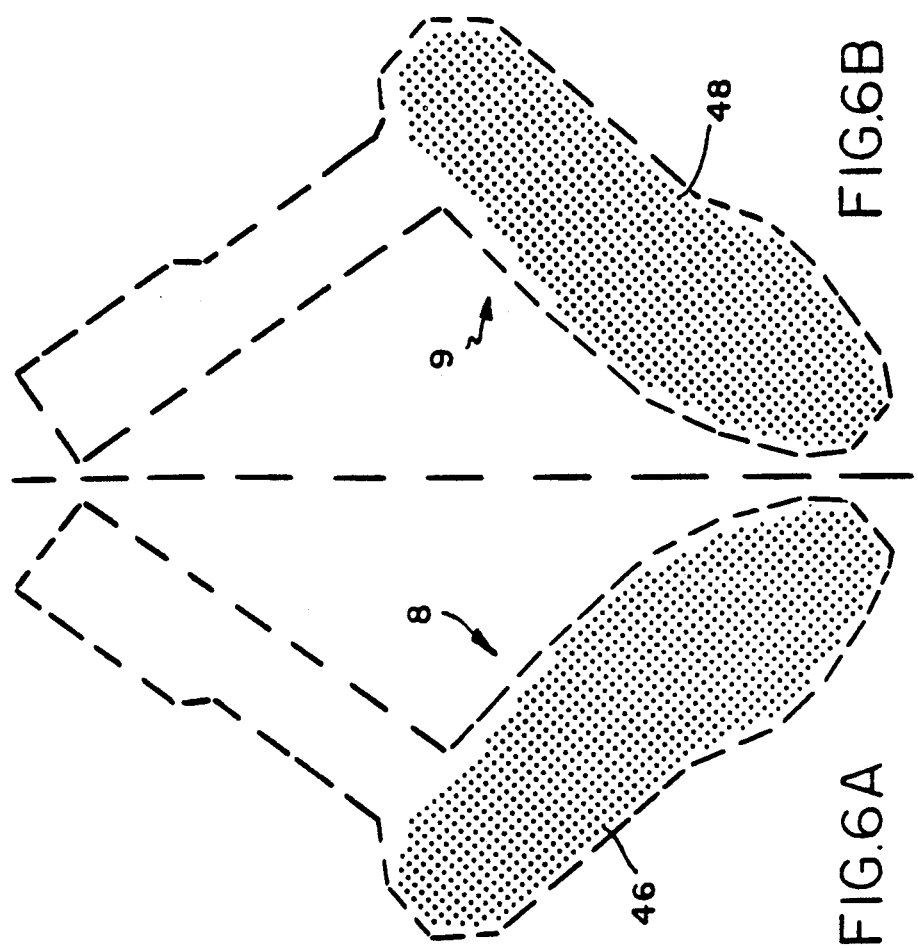
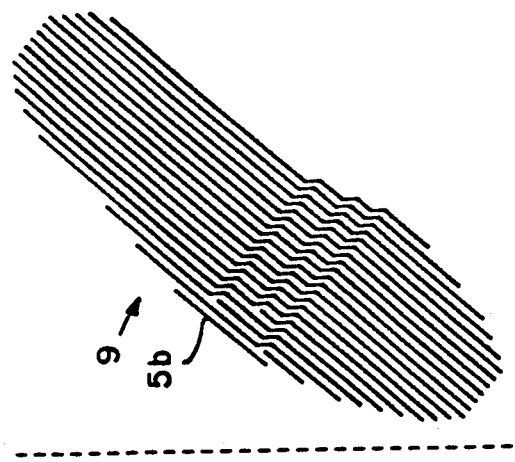
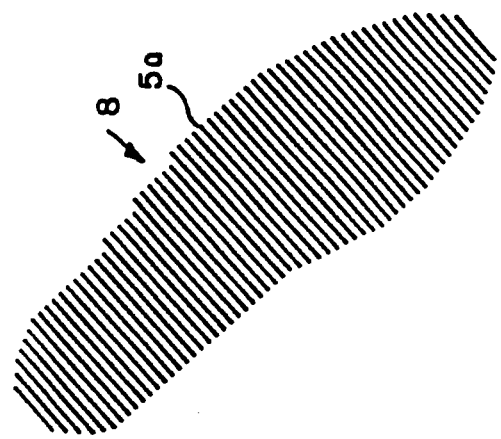

FLEXIBLE TACTILE SENSOR FOR MEASURING FOOT PRESSURE DISTRIBUTIONS AND FOR GASKETS

FIELD OF THE INVENTION

This invention is related to the field of tactile sensors, and more particularly to thin, flexible force and pressure distribution sensors for measuring the force and pressure distribution between opposing objects.

BACKGROUND OF THE INVENTION

There are a number of different types of transducers which are capable of measuring forces and pressures. One type of force transducer includes a sensor having electrodes applied to two, flexible backing sheets which are placed face to face with the electrodes separated by a pressure sensitive resistive material. Examples of such sensors are shown in U.S. Pat. Nos. 4,734,034 and 4,856,993. These two patents show a sensor which includes row and column electrodes on the two backing sheets which are oriented so as to intersect at a plurality of locations. The pressure sensitive material between the electrodes is responsive to forces applied on opposite sides of the sensor and provides a variable resistance at each of the intersections which is representative of the forces at that intersection.

Such sensors have the capability of providing force measurements at many different locations with a spatial resolution on the order of 0.050 inches or less.

The thinness and flexibility of such a sensor allows forces to be measured without significantly disturbing the objects providing those forces. This is particularly important in certain types of instrumentation where the forces being measured may change substantially if the force sensor provides any significant interference to the movement of the objects.

The force sensors shown in the above referenced patents are capable of accurately measuring forces in situations where the forces being applied to the sensors have a small component in a direction parallel to the surface of the sensor. In situations where there are significant shear forces, the performance of the force sensors described in these patents may be degraded. Additionally, the connections with the electrodes are such that the sensor is not easily tailored to different applications requiring differently shaped sensors.

Accordingly, a sensor which would be usable in applications where shear forces are encountered and which additionally is easily modified to fit the needs of different applications would be a desirable improvement.

SUMMARY OF THE INVENTION

The present invention includes a force and pressure sensor in which two backing sheets each have a set of electrodes applied thereto which intersect when the backing sheets are brought into juxtaposition with one another. The conductors connecting the electrodes with external electronics are electrically connected to each electrode intermediate the ends of the electrode. This is done by providing conductors which run between the electrodes and backing sheet and an additional dielectric layer to insulate the conductors from the electrodes. This configuration allows the force and pressure sensor to be trimmed around the edges thereof so that the sensor can be tailored to fit different applications.

The force sensor also includes an adhesive material applied between each of the electrodes in a pattern that allows any air trapped between the two electrode sets to escape from within the sensor while still providing firm attachment between the electrode sets at multiple points to resist shear forces. The thickness of the adhesive layer may be varied to provide different sensitivity. A thicker adhesive layer may be used to provide a threshold force below which no output is provided, while a thinner adhesive layer can be used to effectively provide a pre-load to the sensor. Varying the thickness of the adhesive layer over the surface of the sensor can be used to provide, in a simple manner a sensor which has variable sensitivity at different locations.

The present invention provides significant advantages over previously known force sensors in many applications including particularly the use of a force sensor in a gasket to provide a means for determining the uniformity of pressure across the gasket between the two mating surfaces being sealed by the gasket.

DESCRIPTION OF THE DRAWING

The invention may be more fully understood by way of the examples set forth in the following description of the invention in conjunction with the drawings, of which:

FIGS. 2A and 2B shows the supporting sheet with connecting conductors applied thereto;

FIGS. 3A and 3B shows the insulating layer of the sensor;

FIGS. 4A and 4B show the conductors of the electrodes.

FIGS. 5A and 5B illustrate the pattern of the pressure sensitive material applied to the electrode conductors;

FIGS. 6A and 6B show the adhesive pattern applied to the two halves of the sensor;

DESCRIPTION OF THE PREFERRED EMBODIMENT

In the following example of the present invention, a sensor for measuring forces between a foot and a shoe is used to illustrate the construction and features of the invention. It should be appreciated that the features and advantages described below are equally applicable to other applications where force or pressure is to be measured.

Figure 1A:
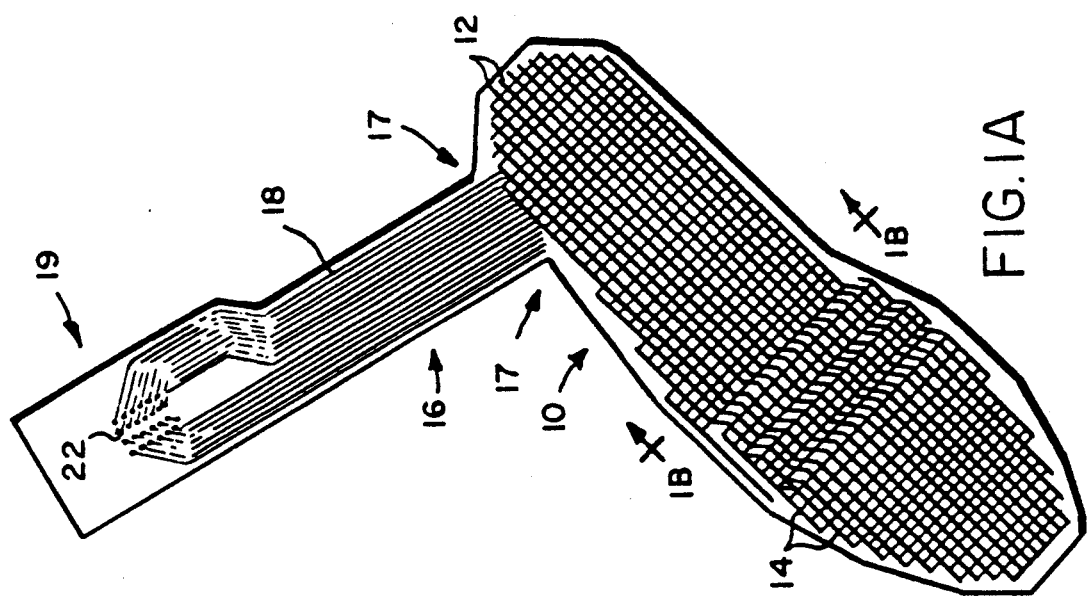
FIG. 1A illustrates the overall configuration of an embodiment of the invention including the electrode positioning.

Referring to FIG. 1A there is shown generally the configuration of a foot pressure distribution sensor constructed in accordance with the present invention. FIG. 1A shows a few of the layers in the sensor. In FIG. 1A, a sensor consisting of intersecting electrodes is provided in foot-shaped area 10. Within area 10, a plurality of electrodes 12 extend in a direction generally lengthwise with respect to the foot, and a second plurality of electrodes 14 extend across the sensor area 10. The electrode sets 12 and 14 will be referred to as column and row electrodes respectively, for convenience. These electrode sets are supported by flexible backing sheets, described in more detail below, and are separated by a pressure sensitive material. Force applied to opposite sides of the sensor area 10 causes the resistance of the pressure sensitive material at each of the intersections between row electrodes 14 and column electrodes 12 to change as a function of the magnitude of the force at each of the intersections.

Each of the row and column electrodes has an associated conductor which is electrically connected to its corresponding electrode and which extends along a stub 16 extending outwardly from the force sensing area 10. In FIG. 1A, a portion of the column electrode conductors 18 is shown extending along stub 16. The column conductors 18 extend upwardly to a terminal area 19 to which a connector for electrically connecting external measuring equipment to each of the electrodes may be attached.

In use, the sensor is placed within a shoe or other orthotic device to measure the forces between a person's foot and the supporting surface beneath the foot. The sensor area 10 would be placed along the sole of the shoe and the stub 16 would extend upwardly along the side of the ankle and leg to allow a connector to be attached to the sensor. As will be described in more detail below, the sensor is constructed so that the peripheral edges of the sensor may be trimmed to fit the force sensing area 10 to the particular size and shape of the foot and shoe to be measured.

Figure 1B:
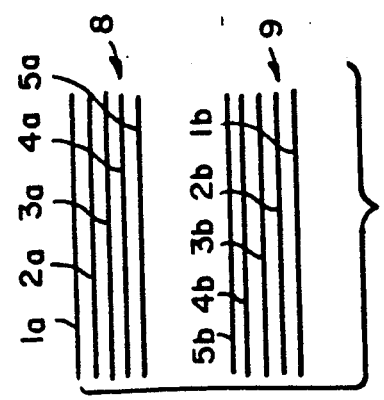
FIG. 1B illustrates the various different layers of the sensors.

The structure shown in FIG. 1A includes a plurality of different layers which are described below, not all of which are shown in FIG. 1A. FIG. 1B illustrates generally the relationship of these layers as they occur in an assembled sensor and represents a cross-section across the sensing area 10 as indicated in FIG. 1A. FIG. 1B shows each of the layers from a side perspective, and each of the numerical designations of the different layers corresponds with the number of the following figure which shows the plan view of that layer. The sensor consists of a "top" portion 8, which includes the row electrodes 14 and a "bottom" portion 9 which includes column electrodes 12. The top and bottom designations are with reference to the figures only, as the sensor operates the same, regardless of its orientation.

Referring to FIG. 1B, the outermost layers 1a and 1b designate the backing sheet material on which the other layers are deposited and which provides the principle physical support for these additional layers. (The backing sheet is shown more fully in FIGS. 2A and 2B.) The backing sheet should be made of an insulating material and should be thin, strong, and flexible. In the preferred embodiment, the backing sheet is made of mylar having a thickness of 0.001" or a similar material. Referring to FIGS. 2A and 2B, backing sheets 1a and 1b are shown, the periphery thereof being represented by the outlines 32 and 30 respectively. The backing sheets are shown as being separate in FIGS. 2A and 2B. In some applications the two backing sheets may be made from a single piece of material and the sensor assembled by folding the backing sheet.

The next layers are conductors 2a and 2b applied to each of the backing sheets. FIGS. 2A and 2B, show the layout of a plurality of conductors 18 and 20 for connecting each of the column and row electrodes respectively to an associated terminal. In FIG. 2A, a plurality of terminals 24 for each of the row electrodes is provided at the end of the stub section 16 on the mylar backing sheet 32. Each of these terminals consists of a circular pad which forms the end of one of the individual conductors 20, which go from each of the terminals 24 along the stub section 16 to the sensing area 10. Within sensing area 10, the row conductors are configured so as to terminate underneath an associated row electrode. The particular arrangement shown in FIG. 2A results in the interconnection between conductors and electrodes being made intermediate the ends of the row electrodes. As will be seen below, this allows the assembled sensor to be trimmed along the edges thereof to provide a custom fit for an individual application. Of course, the sensor cannot be trimmed at the point 17 where the stub 16 connects with the sensor area 10. This, however, makes up a small portion of the periphery of the sensor and does not constitute a significant limitation on the ability to configure the sensor to match different sizes and shapes of feet.

Similarly, in FIG. 2B, a plurality of terminals 22 are each connected to an associated column conductor 18. The column conductors 18 extend along the stub area 16 into the sensor area 10. In sensor area 10, each of the column conductors 18 is configured as shown in FIG. 2B so as to intersect the associated column electrode intermediate the ends thereof.

The row and column conductors are preferably formed upon their respective backing sheets by silk screening a silver conductive ink onto the backing sheet. Inks such as Chomerics 4430 or Acheson Colloids Electroday 47155 with a dry deposition of at least 0.0005" can produce conductors with an overall trace resistance of less than 500 ohms. Typical curing conditions are 3–5 minutes at 160° F. Although suitable conductors can be formed using a variety of techniques (etching, sputter coating, etc.), this method provides an accurate and inexpensive method of reliably reproducing the desired configuration of conductors for the sensor.

The resistances at each of the electrode intersections represent the forces at that intersection and are measured by external electronics not shown or described here. Suitable circuits for performing these measurements are described in detail in the above referenced U.S. Pat. Nos. 4,734,034 and 4,856,993. The measurement circuitry is connected to the sensor by means of a clip on a connector piece which attaches to the terminal area 19. The terminals 22 and 24 are made up of a plurality of dots which are typically larger in dimension than the conductors 18 and 20 so as to provide some tolerance for misalignment between the connector and the pads. The connection to the row terminals 24 is provided through a hole 26 in the backing sheet 1b which supports the opposing column electrodes. Similarly, the connection to the column terminals 22 is provided through a corresponding hole 28 in the backing sheet 1b for the row electrodes.

Referring back to FIG. 1B, each of the row and column conductor sets 2a and 2b have an insulating dielectric layer applied thereto which insulates the conductors from the row and column electrodes except at the ends of the conductors where the conductors are electrically connected to the electrodes. The configuration of the dielectric layers is shown in more detail in FIGS. 3A and 3B. In FIG. 3A, a dielectric layer 3a is applied on top of the row conductors and has the configuration shown. The dielectric layer 3a has a plurality of openings 34 formed therein through which the terminal ends of each of the row conductors 20 are electrically connected to their associated row electrodes. Similarly, the dielectric layer 3b over the column conductors has a plurality of openings 36 therein through which the column conductors and electrodes electrically interconnect. Each of the dielectric layers 3a and 3b has corresponding openings 38 and 40 through which access for the connector to the terminals 22 and 24 is provided. The dielectric layers are typically formed by silk screening a layer of filled thermoplastic epoxy (such as Emerson and Coming ME5146) over the conductors. Typically, a layer at least 0.0002" thicker than the conductors must be applied to provide the necessary electrical isolation. Other methods may also be used to form the dielectric layer, such as the application of ultra violet cured coatings such as Acheson Colloids ML25089 or the use of an intermediate layer of insulating films such as polyester or Kapton.

On top of the dielectric layers 3a and 3b is formed a series of conductive stripes 4a and 4b which form the row and column electrodes respectively. Referring to FIGS. 4A and 4B, the arrangement of the row and column electrodes 4a and 4b is shown. The phantom outlines 100 represent the peripheral edges of the top and bottom portions of the sensor. Row and column electrodes 4a and 4b are made by silk screening a silver ink on top of the dielectric layers in the same manner as the row and column conductors are formed, as described above. In the illustrated embodiment for sensing foot forces, the row and column electrodes are separated by approximately 0.2 inches to provide electrode intersections on 0.2 inch centers. Increased resolution can be easily provided by using a closer electrode spacing. Using conventional silk screening and printing techniques, electrode spacings of 0.050 inches or less can be easily and inexpensively fabricated.

The row electrodes 4a shown in FIG. 4A are composed of a series of straight lines. In FIG. 4B, the column electrodes are shown with a configuration such that some of the electrodes are composed of a series of offset straight lines which are electrically interconnected. This configuration provides a more convenient topology for providing connections between the column electrodes and their respective conductors close to the center of each of the electrodes. This allows the maximum amount of material to be trimmed from the periphery of the sensor in adapting the sensor to different applications. The mapping of a particular row and column electrode intersection to a physical location is easily done by means of a computer or other digital electronics in the measuring circuitry. It should be appreciated that configurations other than those shown may be used, including other types of linear combinations, curves, and circles. For example, row and column electrodes could be replaced with concentric circular electrodes and a plurality of radial electrodes to provide a sensor which directly provides a polar coordinate readout. In the present embodiment, the only limitation to sensor configuration is that each of the "rows" and "columns" intersect at only one location.

A pressure resistive layer must be provided between each of the intersections of the row and column electrodes. In the described embodiment, a pressure resistive material is applied on top of both of the electrode sets. In other words, each row electrode 4a has a stripe of pressure sensitive material 5a applied thereto, and each column electrode 4b has an associated stripe of pressure sensitive material 5b applied. Although the sensor will work with a layer of pressure sensitive material applied to a single electrode set, this method of construction is susceptible to shorts between row and column electrodes which would result from imperfections in the pressure sensitive layer. By applying pressure sensitive materials to both electrodes, the incidence of such defects is reduced. Other arrangement of the pressure sensitive material on the row and column electrodes may be used. Such arrangements are described in more detail in the aforementioned U.S. Pat. No. 4,856,993.

The pressure sensitive material may be applied in a continuous layer over the row and/or column electrodes. However this method of construction will reduce the resistance of the sensor to deformation when subjected to shear stresses. As described below, the adhesive layer in the described embodiment connects the two dielectric layers to one another. When the pressure sensitive material is applied in a continuous sheet, the adhesive layer will adhere less strongly to the sensor portions due to the reduced strength of the pressure sensitive material as compared to the epoxy dielectric.

In the preferred embodiment, the pressure sensitive material may be made of Cho-Shield 4402 ink produced by Chomerics corporation of Woburn, Mass. Other suitable materials are described in the aforementioned patents and include molybdenum-disulfide based inks and other well known pressure sensitive materials.

The two portions of the force sensor including layers 1a through 4a and 1b through 4b respectively are attached to each other by means of one or more adhesive layers therebetween.

During the use of the foot force sensor described, a person may run or do other athletic maneuvers while the sensor is used to measure foot pressure distribution. During these maneuvers, significant shear forces may be applied to the outside surfaces of the sensor which tend to slide the top and bottom layers sideways with respect to one another. Previous sensors have typically had their top and bottom layers interconnected only over a small portion of the force sensing area, such as along only the periphery thereof. When shear forces are applied to such a sensor, the dimensional accuracy of the measurements may be reduced if the row and column electrodes move with respect to one another. In extreme cases, the shear and normal forces may cause the pressure sensitive layer or even the electrodes themselves to be rubbed off causing failure of the sensor. It has been found that providing an adhesive connection between the top and bottom layers over the entire sensor area results in a sensor which can withstand large shear forces without suffering from reduced dimensional accuracy or possible failure.

It has also been found that it is preferable to apply the adhesive layer in a pattern which allows air or other gas which may be present between the top and bottom layers of the sensor to escape when pressure is applied to the sensor. For example, in the described embodiment used for sensing foot pressures, a large amount of force is typically applied over a majority of the area 10 of the force sensor within a very short period of time. A small amount of air trapped within the sensor will literally blow the sensor apart if means to vent this air to the outside is not provided.

In the described embodiment, a plurality of adhesive dots is applied to each of the top and bottom layers as shown in FIG. 6A and 6B. The location of the dots is such that there is an adhesive dot applied to each of the top and bottom layers in the squares defined by the surrounding electrodes, as described below. The preferred embodiment uses a screenable adhesive such as catalog number 205,4714 adhesive available from General Formulations, Inc. of Sparta, Mich. A layer of adhesive between 0.0005 and 0.001 inches thick applied to each half of the sensor has been found to provide a suitable bond. Other adhesives of acrylic or silicone type may be used with the invention. Alternatively, a single adhesive layer may be applied to either the top or bottom layers of the force sensor.

Other patterns for providing venting of gases from the interior of the force sensor may be used, such as linear stripes of adhesive between electrodes. In this case, the adhesive pattern would generally correspond to the areas between the electrodes shown in FIG. 5. However, such a pattern results in a longer path through which gases trapped in the interior must pass to vent to the outside. This increases the likelihood that the sensor may be damaged from a sudden application of force over the entire sensor area. On the other hand using strips provides more adhesive and thus a greater resistance to shear forces. In some examples, such as gaskets where two mating surfaces are slowly brought together by torquing down bolts, the increased resistance to shear forces provided by the additional adhesive may be preferable.

Figure 7:
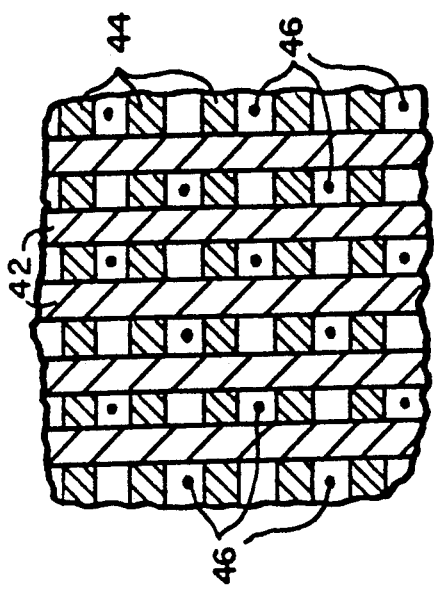
FIG. 7 shows the pattern of applying the adhesive dots.

The pattern in which the adhesive dots 6a and 6b are applied influences the sensitivity of the force sensor. In the described embodiment for sensing foot forces, it has been found that putting adhesive dots in every other square between electrodes increases the sensitivity of the sensor and produces a more suitable sensor. Referring to FIG. 7, this arrangement is shown. In FIG. 7, the vertical bars 42 represent column electrodes, which include both electrode conductors and the pressure sensitive material over the conductors. Similarly, rows 44 represent row electrodes. The adhesive dots 46 are located between every other electrode in a checkerboard pattern.

Figure 8:
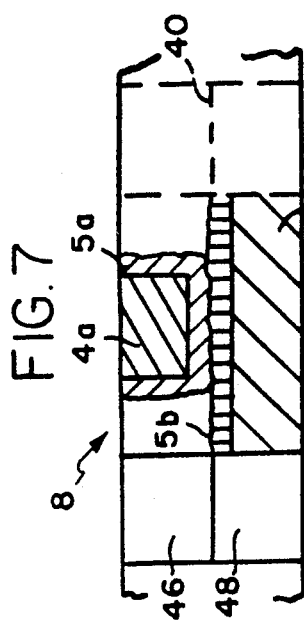
FIG. 8 illustrates how the adhesive acts to keep the force sensor layers separated.

The adhesive dots to ascertain extent act as compression springs holding the top and bottom layers of the sensor apart. Referring to FIG. 8, a row electrode 4a covered with pressure sensitive material 5a is shown crossing a column electrode 4b, also covered with a layer of pressure sensitive material 5b. Two adhesive dots 46 and 48 are shown as they would occur next to the intersection of the row and column electrodes. These adhesive dots are somewhat resilient and resists forces tending to compress the force sensor. If a second pair of adhesive dots is present immediately adjacent the intersection on the other side of the intersection, as shown by dotted lines 40, the resistance of the adhesive dots to compression forces is greatly increased, which reduces the sensitivity of the sensor. Due to the flexibility of the backing material and the other layers making up the sensor, as described herein, omitting every other dot provides sufficient flexibility of the sensor to achieve the desired sensitivity.

The above-described effect may be used to construct a sensor having variable sensitivity over its area. For example, a sensor having more adhesive dots in one are and fewer adhesive dots in another area would provide two levels of sensitivity in the two different areas.

Figure 9:
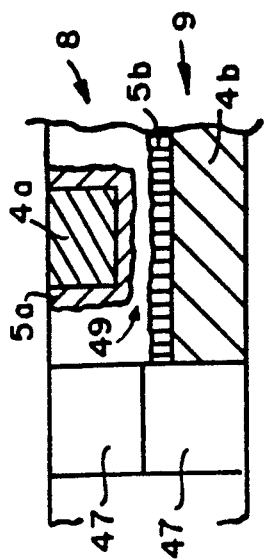
FIG. 9 shows how a thicker adhesive layer can be used to provide a threshold force level.

Another way of varying the sensitivity of the sensor is to vary the thickness of the adhesive as it is applied to the sensor. By applying adhesive layers whose combined thickness is sufficient to separate the top and bottom portions 8 and 9 of the sensor such that there is a small gap between the two layers of pressure sensitive material 5a and 5b, a sensor can be constructed which requires a certain amount of force before the pressure sensitive layers touch and begin conducting. This provides a threshold force which must be exceeded before the sensor will register an output. Such a construction is shown in FIG. 9 wherein two dots 47 have a combined thickness which is sufficient to keep the row and column pressure sensitive materials 5a and 5b separated by a small space 49.

Conversely, the adhesive dots may be applied with a thickness slightly less than the height of the electrode so that the row and column electrodes are pulled together. This effectively provides a pre load to the sensor which increases its sensitivity.

Another application for the force sensor described herein is in gasket applications. Gaskets are made of materials which are somewhat compressive and are placed between two mating surfaces to provide a seal therebetween. Frequently, gaskets are subject to large amounts of pressure. A typical application of a gasket would be in an automobile engine where a gasket is used to provide a seal between the engine block and cylinder head. In such applications, a number of bolts are tightened down to a predetermined torque specification to provide a constant pressure across the mating surfaces which compresses the gasket therebetween to provide the seal. There are many things that can cause such a system to fail. For example, rust or dirt on the threads of the nut and bolt can result in a high torque reading when minimal or no pressure is being applied to the gasket. By providing a force sensor of the typed described above either inside the gasket or as part of the gasket, the compression forces on the gasket over its entire area may be measured to provide a direct indication that the gasket is properly compressed. For example, either or both of the backing sheets may be made from a compressible material to provide both the sealing action of a gasket and the ability to sense pressure distributions. Alternatively, a force sensor as shown in FIGS. 1-7 may be laminated to or otherwise attached to a gasket or gasket material. Other application where such gaskets would be helpful would be in refrigerator doors. Especially in commercial refrigerators, the gaskets sealing such doors may deform and result in significant increases in the cost to maintain the refrigeration. Providing a force sensor as part of such a gasket would allow any gaps in the seal to be immediately detectable.

It should be appreciated that the foregoing description of the invention is by way of example only, and the embodiments described herein may be modified or adapted in applying the principles of the invention to different situations. Accordingly, the embodiments described should not be taken as a limitation on the scope of the present invention, but rather the invention should only be interpreted in accordance with the following claims.

What is claimed is:

1. A sensor for measuring external forces applied to opposite sides thereof, comprising:
    a first plurality of flexible, conductive electrodes attached to and supported by a thin, flexible backing sheet made of an insulative material to provide a first set of electrodes;
    a second plurality of flexible, conductive electrodes attached to and supported by a thin, flexible backing sheet made of an insulative material to provide a second set of electrodes;

the first and second electrode sets being positioned with the first and second electrodes facing one another and arranged so that the electrodes of the first set cross the electrodes of the second set at an angle to create a plurality of electrode intersections where electrodes in the first set cross electrodes in the second set, there being areas on said first and second electrode sets between electrode intersections;

a layer of pressure-sensitive resistive material applied to at least one of the electrode sets in a pattern such that the resistive material lies between the electrodes at each intersection;

an adhesive layer applied to at least one of the first and second electrode sets in said areas between the electrode intersections to secure the first and second electrode sets in said facing relationship; and means for making electrical connection to said first and second electrode sets.

2. The sensor of claim 1 wherein the adhesive layer is applied in a pattern which provides passages where the adhesive layer does not exist to allow air to escape from the interior area of the electrodes sets to the periphery thereof.

3. The sensor of claim 1 wherein the adhesive layer includes a stripe of adhesive material in areas between the electrodes of at least one of the electrode sets.

4. The sensor of claim 1 wherein the adhesive layer includes a plurality of dots of adhesive material in the area between individual electrodes of at least one of the electrode sets.

5. The sensor of claim 1 wherein the adhesive layer includes a plurality of dots in the areas between individual electrodes of at least one of the electrode sets and positioned so that the dots are located in the areas between electrodes in the other of the first and second set of electrodes when the first and second sets are in said facing relationship.

6. The sensor of claim 5 wherein there are quadrilateral areas defined by adjacent pairs of intersecting first and second electrodes, and wherein a dot of adhesive material is present in each of the quadrilateral areas.

7. The sensor of claim 1, 2, 3, 4, 5 or 6 wherein said means for making electrical connection includes a plurality of terminals for connecting the sensor to external circuitry, each terminal being associated with a respective one of the electrodes; and a plurality of connecting conductors, each conductor associate with a respective one of the electrodes, for connecting each terminal to its associated electrode, the conductors being connected to their associated electrodes intermediate the ends thereof.

8. The sensor of claim 7 wherein the conductors are arranged so that the sensor may be trimmed around at least a majority of the periphery thereof without interrupting the connections between the conductors and said associated electrode.

9. The sensor of claims 1, 2, 3, 4, 5 or 6 wherein at least one of the electrode sets further includes:

a plurality of terminals attached to the flexible backing sheet, each associated with a respective one of the electrodes of that electrode set, for connecting the sensor to external circuitry;

a plurality of connecting conductors attached to said backing sheet, each conductor associated with a respective one of the electrodes, for connecting each terminal to its associated electrode, the conductors being connected to their associated electrodes intermediate the ends thereof; and a thin, flexible insulating sheet applied over the plurality of connecting conductors and including holes therethrough through which electrical connection is made between each of the connecting conductors and the associated electrode.

10. The sensor of claim 9 wherein the conductors are connected to their associated electrodes at a point intermediate the ends of the electrode.

11. The sensor of claim 9 wherein the sensor has an outer periphery, and wherein the connecting conductors are arranged so that the sensor may be trimmed around at least a majority of said outer periphery without interrupting the connections between the conductors and associated electrodes.

12. The sensor of claim 9 wherein the thickness of the adhesive layer is sufficient to keep the opposing electrodes spaced apart at said intersections in the absence of an external force.

13. The sensor of claim 9 wherein the thickness of the adhesive layer is sufficiently thin so that opposing electrodes at each intersection are maintained in contact with each other with a pre-load force.

14. The sensor of claims 1, 2, 3, 4, 5 or 6 wherein both of the electrode sets further include:

a plurality of terminals attached to the flexible backing sheet, each associated with a respective one of the electrodes of that electrode set, for connecting the sensor to external circuitry;

a plurality of connecting conductors attached to said backing sheet, each conductor associated with a respective one of the electrodes, for connecting each terminal to its associated electrode, the conductors being connected to their associated electrodes intermediate the ends thereof; and a thin, flexible insulating sheet applied over the plurality of connecting conductors and including holes therethrough through which electrical connection is made between each of the connecting conductors and the associated electrode.

15. The sensor of claim 1, 2, 3, 4, 5 or 6 wherein the thickness of the adhesive layer is sufficient to keep the electrodes at each electrode intersection spaced apart in the absence of an external force.

16. The sensor of claims 1, 2, 3, 4, 5 or 6 wherein the thickness of the adhesive layer is sufficiently thin so that opposing electrodes at each intersection are maintained in contact with each other with a pre-load force.

17. A sensor for measuring external forces applied to opposite sides thereof, comprising:

a plurality of flexible, conductive electrodes attached to and supported by thin, flexible backing sheet made of an insulative material to provide a first set of electrodes;

a second plurality of flexible, conductive electrodes attached to and supported by thin, flexible backing sheet made of an insulative material to provide a second set of electrodes;

the first and second electrode sets being positioned with the first and second electrodes facing one another and arranged so that the electrodes of the first set cross the electrodes of the second set at an angle to create a plurality of electrode intersections where electrodes in the first set cross electrodes in the second set;

a layer of pressure-sensitive resistive material applied to at least one of the electrode sets such that the resistive material lies between the electrodes at each intersection;

means for securing the first and second electrode sets in said facing relationship;

a plurality of terminals attached to the flexible backing sheet for at least one of the electrode sets, each of said terminals being associated with a respective one of the electrodes of the electrode set, the terminals connecting the sensor to external circuitry;

a plurality of connecting conductors attached to said backing sheet, each conductor associated with a respective one of the electrodes, for connecting each terminal to its associated electrode, the conductors being connected to their associated electrodes intermediate the ends thereof; and a thin, flexible insulating sheet applied over the plurality of connecting conductors, said insulating sheet having holes therethrough through which electrical connection is made between each of the connecting conductors and the associated electrode.

18. The sensor of claim 17 wherein the sensor has an outer periphery, and wherein the connecting conductors are arranged so that the sensor is trimmable around at least a majority of said outer periphery without interrupting the connections between the conductors and the associated electrodes.

* * * * *